(12) United States Patent
Murray et al.

(10) Patent No.: US 11,718,597 B2
(45) Date of Patent: Aug. 8, 2023

(54) METHOD FOR PREPARING A TETRAFLUORO-1,2-EPOXYPROPANE

(71) Applicant: MEXICHEM FLUOR S.A.DE C.V., San Luis Potosi (MX)

(72) Inventors: James Henry Murray, Chesire (GB); Andrew Paul Sharratt, Chesire (GB)

(73) Assignee: MEXICHEM FLUOR S.A.DE C.V., San Luis Potosi (MX)

( * ) Notice: Subject to any disclaimer, the term of this patent is extended or adjusted under 35 U.S.C. 154(b) by 0 days.

(21) Appl. No.: 17/829,598

(22) Filed: Jun. 1, 2022

(65) Prior Publication Data

US 2022/0289701 A1 Sep. 15, 2022

Related U.S. Application Data

(62) Division of application No. 16/608,149, filed as application No. PCT/GB2018/051124 on Apr. 27, 2018, now Pat. No. 11,377,432.

(30) Foreign Application Priority Data

Apr. 27, 2017 (GB) .................................. 1706721

(51) Int. Cl.
*C07D 301/26* (2006.01)
*C08G 65/22* (2006.01)
(Continued)

(52) U.S. Cl.
CPC ......... *C07D 301/26* (2013.01); *C08G 65/226* (2013.01); *C10M 107/38* (2013.01); *C10M 2213/043* (2013.01); *C10N 2040/30* (2013.01)

(58) Field of Classification Search
CPC .. C07D 301/26; C07D 303/08; C07D 303/48; C08G 65/226; C08G 65/007;
(Continued)

(56) References Cited

U.S. PATENT DOCUMENTS

| | | |
|---|---|---|
| 2007/0282137 A1 | 12/2007 | Ramachandran et al. |
| 2008/0114193 A1 | 5/2008 | Ramachandran et al. |
| 2009/0161727 A1 | 6/2009 | Wielgus et al. |

FOREIGN PATENT DOCUMENTS

| | | |
|---|---|---|
| EP | 0062325 | 10/1982 |
| EP | 1698650 | 9/2006 |

(Continued)

OTHER PUBLICATIONS

Cramer, Christopher J. et al., "Perfluorocarbenes Produced by Thermal Cracking. Barriers to Generation and Rearrangement" Journal of Organic Chemistry (1999) 64: 4850-4859.
(Continued)

*Primary Examiner* — Cephia D Toomer
(74) *Attorney, Agent, or Firm* — Crowell & Moring, LLP; Yuezhong Feng

(57) ABSTRACT

A method for preparing a tetrafluoro-1,2-epoxypropane comprising reacting a 3-acetoxy-2-bromo-tetrafluoropropane with an alkaline or alkaline earth metal hydroxide solution to provide a tetrafluoro-1,2-epoxypropane, and partially fluorinated polyethers of formula $[OCRR_1CR_2R_3]_n$ wherein n is from 5 to 100, R is F or H, $R_1$ is $CF_3$, $R_2$ is F or H and $R_3$ is H.

16 Claims, 9 Drawing Sheets

(51) Int. Cl.
*C10M 107/38* (2006.01)
*C10N 40/30* (2006.01)

(58) Field of Classification Search
CPC .............. C08G 65/22; C10M 107/38; C10M 2213/043; C10M 147/04; C10N 2040/30
See application file for complete search history.

(56) References Cited

FOREIGN PATENT DOCUMENTS

| JP | 5051445 | 3/1993 | |
| JP | 9110980 | 4/1997 | |
| JP | 4570788 | * 10/2010 | |
| WO | WO 2007/143154 | 12/2007 | |
| WO | WO 2010/101337 | 9/2010 | |
| WO | WO 2016/080484 | 8/2017 | |

OTHER PUBLICATIONS

McBree, E.T. et al., "1,3,3,3-Tetrafluoropropylene Oxide" (1953) 75: 4091-4092.
Schuster, Paul et al., "Biotransformation of 2,3,3,3-tetrafluoropropene (HFO-1234yf) in rabbits" Toxicology and Applied Pharmacology (2010) 244: 247-253.
Thomas, Renee M. et al., "Enantioselective Epoxide Polymerization Using a Bimetallic Cobalt Catalyst" Journal of the American Chemical Society (2010) 132(46): 16520-16525.
Hagiwara et al., "Polymerization of 3,3,3-trifluoro-1,2-epoxypropane with organozinc compounds and alkali metal alkoxides," *Makromol. Chem. Rapid Commun.*, 13 (1992), pp. 363-370.
Schuster et al., "Biotransformation of 2,3,3,3-tetrafluoropropene (HF0-1234yf)," *Toxicology and Applied Pharmacology*, 233 (2008), pp. 323-332.
Ramachandra et al., "Preparative-scale synthesis of 3,3,3-trifluoropropene oxide," *Journal of Fluorine Chemistry* 128 (2007) pp. 1255-1259.
Lermontov et al., "Novel method for the synthesis of (trifluoromethyl)oxirane," *Russian Chemical Bulletin, International Edition*, 51:3 (2002) pp. 550-551.
Nguyen et al., "Transformation de l'hexafluoropropene en alcool trifluoroallylique, précurseur des a-fluoroacrylatesJ," *Journal of Fluorine Chemistry*, 74 (1995) pp. 273-277.
Hemer et al., "Pluorohalogeno Compounds. I. The Grignard Reaction Of SomeFluorohalogenoethanes," *Journal of Fluorine Chemistry*, 26 (1984) pp. 467-479.
Chittaranjan et al., "Alkylation of Malonic Ester by Ethylene Oxide Catalyzed by Anhydrous A1C13," *Journal of American. Chemistry. Society.*, 75 (1953), pp. 4098-4099.
English translation of Second Office Action dated Feb. 10, 2023 (5 pages) out of corresponding Chinese Patent Application 201880027469.0.
Article (Excerpt), Ji Zhizhong et al., "*Chemical Pharmaceutical Technology*", Chemical Industry Press, p. 17, Jul. 1980, (4 pages total including English translation).

* cited by examiner

METHOD FOR PREPARING A TETRAFLUORO-1,2-EPOXYPROPANE

This application is a divisional of U.S. patent application Ser. No. 16/608,149, filed Oct. 24, 2019, which is a U.S. National Phase under 35 U.S.C. § 371 of International Application No. PCT/GB2018/051124, filed Apr. 27, 2018, designating the United States and published in English on Nov. 1, 2018, as WO 2018/197897, which claims priority to United Kingdom Application No. 1706721.6, filed Apr. 27, 2017, each of which is incorporated by reference in its entirety.

FIELD

The present invention relates to methods of preparing tetrafluoro-1,2-epoxypropanes and compounds which are 2,3,3,3-tetrafluoro-1,2-epoxypropane and fluorinated polyether polymers derived from tetrafluoro-1,2-epoxypropanes such as 2,3,3,3-tetrafluoro-1,2-epoxypropane and other related tetrafluoropropene epoxides, such as 1,3,3,3-tetrafluoro-1,2-epoxypropane.

The present invention also relates to 3-acetoxy-2-bromo-1,1,1,2-tetrafluoropropane and 2-bromo-1,1,1,2-tetrafluoropropan-3-ol, methods of preparing 3-acetoxy-2-bromo-tetrafluoropropanes from tetrafluoropropenes, such as 3-acetoxy-2-bromo-1,1,1,2-tetrafluoropropene from 2,3,3,3-tetrafluoropropene, methods of preparing 2-bromo-tetrafluoropropan-3-ols from 3-acetoxy-2-bromo-tetrafluoropropanes, such as 2-bromo-1,1,1,2-tetrafluoropropan-3-ol from 3-acetoxy-2-bromo-1,1,1,2-tetrafluoropropane, methods of preparing tetrafluoro-1,2-epoxypropanes from 2-bromo-tetrafluoropropan-3-ols, and the preparation of partially fluorinated polyether polymers derived from 2,3,3,3-tetrafluoro-1,2-epoxypropane and other related tetrafluoropropene epoxides, such as 1,3,3,3-tetrafluoro-1,2-epoxypropane.

BACKGROUND

Polyethers are an important class of materials with significant commercial value. They are commonly used to manufacture products such as foams, sealants, surfactants, elastomers and biomedical components.

The polymerisation of fluorinated epoxides is known in the art. The ring opening polymerisation of fluorinated epoxides can produce oily or grease-like oligomers, which can be utilized for vacuum pump oil and lubricants of high performance.

The polymerisation of 3,3,3-trifluoro-1,2-epoxypropane is described in, for example, J. Am. Chem. Soc., 2010, 132, 16520 to 16525, Makromol. Chem., Rapid Commun., 13, 363 to 370, JP05-051445 and JP09-110980.

The polymerisation of hexafluoropropylene oxide is described in, for example, EP0062325 and WO2010/101337.

The listing or discussion of a prior-published document in this specification should not necessarily be taken as an acknowledgement that the document is part of the state of the art or is common general knowledge.

To date the polymerisation of tetrafluoropropene epoxides has not been reported.

Methods of obtaining tetrafluoropropene epoxides, such as 2,3,3,3-tetrafluoro-1,2-epoxypropane and 1,3,3,3-tetrafluoro-1,2-epoxypropane, and methods of polymerising these epoxides are desirable.

SUMMARY

The present invention provides a partially fluorinated polyether of formula $[OCRR_1CR_2R_3]_n$ wherein n is 5 to 100 such as 20 to 60, R is F or H, $R_1$ is $CF_3$, $R_2$ is F or H and $R_3$ is H, a method for the preparation of such polyethers, such as poly(2,3,3,3-tetrafluoro-1,2-epoxypropane) and other poly(tetrafluoro-1,2-epoxypropanes) such as poly(1,3,3,3-tetrafluoro-1,2-epoxypropane).

Tetrafluoro-1,2-epoxypropanes may be prepared by dehydrobromination of 2-bromo-tetrafluoropropan-3-ol, which in turn may be prepared from 3-acetoxy-2-bromo-tetrafluoropropane. 2,3,3,3-tetrafluoro-1,2-epoxypropane may be prepared by dehydrobromination of 2-bromo-1,1,1,2-tetrafluoropropan-3-ol, which in turn may be prepared from 3-acetoxy-2-bromo-1,1,1,2-tetrafluoropropane.

The present invention also provides a compound 3-acetoxy-2-bromo-1,1,1,2-tetrafluoropropane.

The present invention also provides a method for the preparation of 3-acetoxy-2-bromo-1,1,1,2-tetrafluoropropane, and other 3-acetoxy-2-bromo-tetrafluoropropanes such as 3-acetoxy-2-bromo-1,1,1,3-tetrafluoropropane.

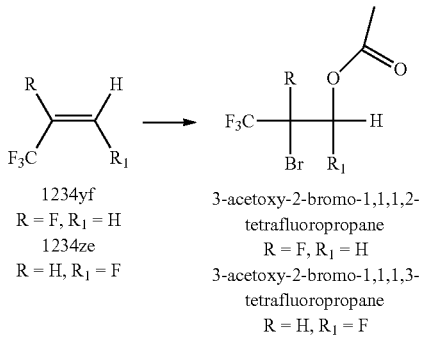

1234yf
R = F, $R_1$ = H
1234ze
R = H, $R_1$ = F 3-acetoxy-2-bromo-1,1,1,2-
tetrafluoropropane
R = F, $R_1$ = H
3-acetoxy-2-bromo-1,1,1,3-
tetrafluoropropane
R = H, $R_1$ = F 3-acetoxy-2-bromo-tetrafluoropropanes may be prepared by reacting a tetrafluoropropene with a brominating agent in the presence of an acylating agent and an acid that has a pKa of less than about 3 in a bromo-oxidation reaction.

DETAILED DESCRIPTION

By the term 'acid that has a pKa of less than about 3', we include acids such as sulphuric acid, hydroiodic acid, hydrobromic acid, perchloric acid, hydrochloric acid, p-toluenesulfonic acid, methanesulfonic acid or mixtures thereof.

By the term 'acylating agent' we mean any compound capable of adding an acyl group to a compound, such as an acyl halide or an acyl anhydride. Examples of acylating agents that may be used in the method of the present invention include, but are not limited to, acetic acid, acetyl chloride or acetic anhydride.

By the term 'brominating agent', we include the meaning of any compound that can act as a source to add bromine across a double bond, such as N-bromosuccinimide or bromine.

For example, 3-acetoxy-2-bromo-1,1,1,2-tetrafluoropropane may be prepared by reacting 2,3,3,3-tetrafluoropropene with N-bromosuccinimide in the presence of acetic acid and sulphuric acid in a bromo-oxidation reaction.

2,3,3,3-tetrafluoropropene is also known as 1234yf. Hereinafter, unless otherwise stated 2,3,3,3-tetrafluoropropene will be referred to as 1234yf.

1,3,3,3-tetrafluoropropene is also known as 1234ze. Hereinafter, unless otherwise stated 1,3,3,3-tetrafluoropropene will be referred to as 1234ze. The description of 1234ze also includes the two (E) and (Z) geometric isomers of 1234ze. As used herein, "1234ze" means any composition containing from 100% E isomer (0% Z isomer) to 100% Z isomer (0% E isomer). Examples of 1234ze materials that may be used in the include those in which the bulk of the material is the E isomer, for example more that 50% E isomer, more preferably >90% E isomer, still more preferably >99% E isomer.

In the present invention, the bromo-oxidation of tetrafluoropropenes such as 1234yf or 1234ze, may be carried out batch-wise or continuously. Any suitable apparatus may be used, such as a static mixer, a tubular reactor, a stirred tank reactor or a stirred vapour-liquid disengagement vessel.

The 3-acetoxy-2-bromo-tetrafluoropropane product from the bromo-oxidation reaction may be subjected to one or more purification steps. The purification may be achieved, for example, by separation of the desired product or reagents by one or more distillation, condensation or phase separation steps and/or by scrubbing with water or aqueous base and drying with e.g. molecular sieves, zeolites or other desiccants. Any unreacted tetrafluoropropene, such as 1234yf or 1234ze, may be recycled back into the reaction.

The bromo-oxidation reaction typically converts at least about 20% of the starting tetrafluoropropene into 3-acetoxy-2-bromo-tetrafluoropropane, preferably at least about 40%, such as at least about 60%, at least about 70% or at least about 80%, for example, at least about 90%.

The bromo-oxidation reaction is typically conducted in the liquid phase at atmospheric pressure. A temperature of from about 60 to about 100° C. may be used, e.g. from about 70 to about 90° C., such as about 80° C. Lower and higher temperatures can be used. Typically, lower or higher temperatures are used if the reaction pressure is higher or lower than atmospheric pressure, respectively.

Any suitable solvent may be used or the reaction may be conducted in the absence of any solvent. Preferably, no solvent is required, by this we mean that the reagents may act as a solvent, but no additional solvent is used. By suitable solvent we mean a solvent in which the reactants dissolve. The solvent should be stable to the bromo-oxidation reaction and should not react with either the reactants or products within the taught ranges of temperature, pressure etc.

At room temperature and pressure, tetrafluoropropenes such as 1234yf and 1234ze, are gases. They can be fed to the solution comprising an acylating agent, such as acetic acid; sulphuric acid and a brominating agent, such as N-bromosuccinimide as either a liquid or vapour.

The present invention also provides a compound 2-bromo-1,1,1,2-tetrafluoropropan-3-ol.

The present invention also provides a method for the preparation of 2-bromo-1,1,1,2-tetrafluoropropan-3-ol from 3-acetoxy-2-bromo-1,1,1,2-tetrafluoropropane, and other 2-bromo-tetrafluoropropan-3-ols from 3-acetoxy-2-bromo-tetrafluoropropanes, such as 2-bromo-1,1,1,3-tetrafluoropropan-3-ol from 3-acetoxy-2-bromo-1,1,1,3-tetrafluoropropane.

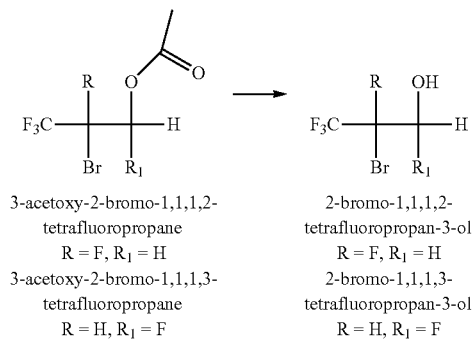

3-acetoxy-2-bromo-1,1,1,2-
tetrafluoropropane
R = F, R₁ = H
3-acetoxy-2-bromo-1,1,1,3-
tetrafluoropropane
R = H, R₁ = F 2-bromo-1,1,1,2-
tetrafluoropropan-3-ol
R = F, R₁ = H
2-bromo-1,1,1,3-
tetrafluoropropan-3-ol
R = H, R₁ = F 2-bromo-tetrafluoropropan-3-ols may be prepared by hydrolysing 3-acetoxy-2-bromo-tetrafluoropropanes with an acidic species in an aqueous solution.

By the term 'an acidic species', we include the meaning of a compound or molecule with a pKa of less than 7, such as a pKa of less than about 5 or less than about 3.

2-bromo-1,1,1,2-tetrafluoropropan-3-ol may be prepared by hydrolysing the 3-acetoxy-2-bromo-1,1,1,2-tetrafluoropropane with an acidic species e.g. sulphuric acid in an aqueous solution.

Aqueous solutions of the acid are typically prepared from concentrated solutions of acid diluted with water, e.g. deionised water. Such preparation would be well known to the person skilled in the art.

In the present invention, the hydrolysis of the 3-acetoxy-2-bromo-tetrafluoropropane may be carried out batch-wise or continuously. Any suitable apparatus may be used, such as a static mixer, a tubular reactor, a stirred tank reactor or a stirred vapour-liquid disengagement vessel.

The 2-bromo-tetrafluoropropan-3-ol product from the hydrolysis reaction may be subjected to one or more purification steps. The purification may be achieved, for example, by separation of the desired product(s) or reagents by one or more distillation, condensation or phase separation steps and/or by scrubbing with water or aqueous base and drying with e.g. molecular sieves, zeolites or other desiccants. Any 3-acetoxy-2-bromo-tetrafluoropropane that remains unreacted may be recycled back into the reaction.

The hydrolysis reaction typically converts at least about 40% of the starting 3-acetoxy-2-bromo-tetrafluoropropane into the 2-bromo-tetrafluoropropan-3-ol, preferably at least about 60%, for example, about 80%.

The hydrolysis reaction is typically conducted in the liquid phase at atmospheric pressure. Any temperature and pressure combination that enables the reaction to reflux may be used. For example, a temperature of from about 60° C. to about 400° C., at atmospheric pressure, may be used, e.g. from about 100° C. to about 350° C., such as about 330° C. Lower and higher temperatures may be used. Typically, lower or higher temperatures are used if the reaction pressure is higher or lower than atmospheric pressure, respectively.

Any suitable solvent may be used or the reaction can be conducted in the absence of any solvent. Preferably, no solvent is required, by this we mean that the reagents may act as a solvent, but no additional solvent is used. By suitable solvent we mean a solvent in which the reactants dissolve. The solvent should be stable to the hydrolysis reaction and should not react with either the reactants or products within the taught ranges of temperature, pressure etc.

Those skilled in the art will appreciate that under the appropriate conditions the bromo-oxidation and hydrolysis steps may be carried out simultaneously to form the required 2-bromo-tetrafluoropropan-3-ol product.

In an aspect of the invention, the method of preparing 2-bromo-tetrafluoropropan-3-ols by the bromo-oxidation of 3-acetoxy-2-bromo-tetrafluoropropanes uses 3-acetoxy-2-bromo-tetrafluoropropanes prepared as previously described.

The present invention provides a method for preparing a tetrafluoro-1,2-epoxypropane comprising reacting a 2-bromo-tetrafluoropropan-3-ol with an alkaline or alkaline earth metal hydroxide solution. For example, the invention provides a method for the preparation of 2,3,3,3-tetrafluoro-1,2-epoxypropane from 2-bromo-1,1,1,2-tetrafluoropropan-3-ol and other tetrafluoro-1,2-epoxypropanes from 2-bromo-tetrafluoropropan-3-ols, such as 1,3,3,3-tetrafluoro-1,2-epoxypropane from 2-bromo-1,1,1,3-tetrafluoropropan-3-ol.

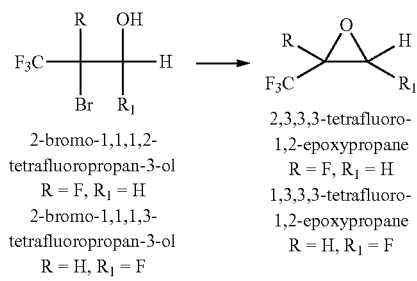

2-bromo-1,1,1,2-
tetrafluoropropan-3-ol
R = F, R$_1$ = H
2-bromo-1,1,1,3-
tetrafluoropropan-3-ol
R = H, R$_1$ = F 2,3,3,3-tetrafluoro-
1,2-epoxypropane
R = F, R$_1$ = H
1,3,3,3-tetrafluoro-
1,2-epoxypropane
R = H, R$_1$ = F Tetrafluoro-1,2-epoxypropanes may be prepared by dehydrobromination of 2-bromo-tetrafluoropropan-3-ols.

2,3,3,3-tetrafluoro-1,2-epoxypropane may be prepared by dehydrobromination of the 2-bromo-1,1,1,2-tetrafluoropropan-3-ol. The present invention also provides a compound which is 2,3,3,3-tetrafluoro-1,2-epoxypropane.

Typically, the dehydrobromination comprises reacting the 2-bromo-1,1,1,2-tetrafluoropropan-3-ol or 2-bromo-1,1,1,3-tetrafluoropropan-3-ol with an alkaline or alkaline earth metal hydroxide e.g. sodium or potassium hydroxide in an aqueous solution, e.g. with deionised water.

In the present invention, the dehydrobromination of 2-bromo-tetrafluoropropan-3-ols may be carried out batchwise or continuously. Any suitable apparatus may be used, such as a static mixer, a tubular reactor, a stirred tank reactor or a stirred vapour-liquid disengagement vessel. In a preferred embodiment the tetrafluoro-1,2-epoxypropane is removed from the reactor by distillation as it is formed. This can maximise the yield and prevent polymerisation in situ.

The dehydrobromination of 2-bromo-tetrafluoropropan-3-ols may also be carried out using a multi-phase reactor system wherein the organic species are predominantly soluble in one phase and the inorganic species another. Reaction occurs by transfer of reactants between phases which can be facilitated with phase transfer catalysts such as Crown ethers or Cryptands or surfactants such as Aliquat 336. Such a method of contacting is believed to help prevent unwanted in situ polymerisation of the epoxide product.

The crude tetrafluoro-1,2-epoxypropane product from the dehydrobromination reaction may be subjected to one or more purification steps. The purification may be achieved, for example, by separation of the desired product(s) or reagents by one or more of distillation, condensation or phase separation steps and/or by scrubbing with water or aqueous base and drying with e.g. molecular sieves, zeolites or other desiccants. Any 2-bromo-tetrafluoropropan-3-ol that remains unreacted may be recycled back into the reaction.

The dehydrobromination reaction is typically conducted in the liquid phase. A temperature of from about 60° C. to about 120° C. may be used, e.g. from about 80° C. to about 110° C., such as about 90° C. or about 100° C. Lower and higher temperatures may be used. Typically, lower or higher temperatures are used if the reaction pressure is higher or lower than atmospheric pressure.

The reaction is typically conducted in an aqueous environment. Any suitable additional solvent may be used or the reaction can be conducted in the absence of any additional solvent. Preferably, no additional solvent is required, by which we mean that the reagents may act as a solvent, with no additional solvent is used. By suitable we include the meaning of a solvent in which the reactant(s) dissolve at least partially. The additional solvent should be stable to the dehydrobromination and should not react with either the reactants or products within the taught ranges of temperature, pressure etc.

The present invention also provides a method for the preparation of tetrafluoro-1,2-epoxypropanes, formed directly from 3-acetoxy-2-bromo-tetrafluoropropanes, such as 2,3,3,3-tetrafluoro-1,2-epoxypropane from 3-acetoxy-2-bromo-1,1,1,2-tetrafluoropropane, by treatment of the 3-acetoxy-2-bromo-tetrafluoropropane with an aqueous alkaline or alkaline earth metal hydroxide solution, e.g. sodium hydroxide.

In the present invention, the alkaline hydrolysis of 3-acetoxy-2-bromo-tetrafluoropropane may be carried out batchwise or continuously. Any suitable apparatus may be used, such as a static mixer, a tubular reactor, a stirred tank reactor or a stirred vapour-liquid disengagement vessel.

The tetrafluoro-1,2-epoxypropane product from the hydrolysis reaction may be subjected to one or more purification steps. The purification may be achieved, for example, by separation of the desired product(s) or reagents by one or more of distillation, condensation or phase separation steps. Any 3-acetoxy-2-bromo-tetrafluoropropane that remains unreacted may be recycled back into the reaction.

The hydrolysis reaction is typically conducted in the liquid phase. A temperature of from about 60° C. to about 120° C. may be used, e.g. from about 80° C. to about 110° C., such as about 90° C. or about 100° C. Lower and higher temperatures may be used. Typically, lower or higher temperatures are used if the reaction pressure is higher or lower than atmospheric pressure.

The reaction is typically conducted in an aqueous environment. Any suitable additional solvent may be used or the reaction can be conducted in the absence of any additional solvent. Preferably, no additional solvent is required, by which we mean that the reagent(s) may act as a solvent, with no additional solvent is used. By suitable we include the meaning of a solvent in which the reactants dissolve at least partially. The additional solvent should be stable to the hydrolysis and should not react with either the reactants or products within the taught ranges of temperature, pressure etc.

In an aspect of the invention, the method of preparing tetrafluoro-1,2-epoxypropanes by the dehydrobromination of 2-bromo-tetrafluoropropan-3-ols uses 2-bromo-tetrafluoropropan-3-ols or 3-acetoxy-2-bromo-tetrafluoropropanes prepared as previously described.

The present invention also provides a process for the preparation of partially fluorinated polyether polymers via the polymerisation of tetrafluoropropene oxides, such as 1,3,3,3-tetrafluoro-1,2-epoxypropane or 2,3,3,3-tetrafluoro-1,2-epoxypropane.

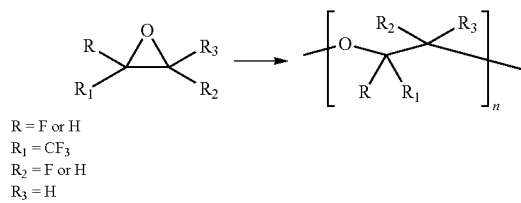

R = F or H
$R_1$ = $CF_3$
$R_2$ = F or H
$R_3$ = H

For 1,3,3,3-tetrafluoro-1,2-epoxypropane and poly(1,3,3,3-tetrafluoro-1,2-epoxypropane) R is H, $R_1$ is $CF_3$, $R_2$ is H and $R_3$ is F and n is from 5 to 100, such as 20 to 60. For 2,3,3,3-tetrafluoro-1,2-epoxypropane and poly(2,3,3,3-tetrafluoro-1,2-epoxypropane) R is F, $R_1$ is $CF_3$, $R_2$ is H and $R_3$ is H and n is from 5 to 100, such as 20 to 60.

The present invention also provides partially fluorinated polyether polymers obtainable by the polymerisation of tetrafluoropropene oxides, such as 1,3,3,3-tetrafluoro-1,2-epoxypropane or 2,3,3,3-tetrafluoro-1,2-epoxypropane. For example, the present invention provides poly(1,3,3,3-tetrafluoro-1,2-epoxypropane) and poly(2,3,3,3-tetrafluoro-1,2-epoxypropane).

The polymerisation of the tetrafluoropropene oxides is preferably a ring opening polymerisation, producing polymers of molecular weight of from about 200 to about 250000. Oligomers, dimers and trimers can also be obtained.

The ring opening polymerisation is typically conducted using a cationic, anionic or organometallic mediated polymerisation, although other polymerisation methods may be used and would be known to the person skilled in the art.

An example of cationic mediated polymerisation is through the use of acids such as $H_2SO_4$, $HOSO_2CF_3$ and $HClO_4$.

Examples of anionic mediated polymerisation include the use of alkali metal tert-butoxides, such as tert-$C_4H_9$OLi, tert-$C_4H_9$OK, tert-$C_4H_9$ORb, and tert-$C_4H_9$OCs, potassium hydroxide, metal chlorides such as aluminium chloride or iron chloride, and metal fluorides such as caesium fluoride or potassium fluoride.

Examples of organometallic mediated polymerisation include the use of organozinc compounds, such as $Zn(C_2H_5)_2$, $(C_2H_5ZnOCH_3)_4$, $[Zn(OCH_3)_2 \cdot (C_2H_5ZnOCH_3)_6]$, $(Zn(OCH_3)_2)_n$ and $[C_2H_5ZnMP]_2[ZnMP_2]_2$ (wherein MP is $CH_3OCH_2CH(CH_3)O$—); and organoaluminium compounds such as trimethylaluminium, triethylaluminium or triisobutylaluminium.

It is also possible to perform the polymerisation reaction stereospecifically, using regio-, enantio- or iso-selective catalysts, such as the bimetallic cobalt catalyst described by Thomas et al, in J. Am. Chem. Soc., 2010, 132, 16520-16525.

In the present invention, the polymerisation may be carried out batch-wise or continuously. Any suitable apparatus may be used, such as a static mixer, a tubular reactor, a stirred tank reactor or a stirred vapour-liquid disengagement vessel.

Typically, the polymerisation is conducted in the absence of oxygen, such as under a nitrogen atmosphere.

The product from the polymerisation of either 1,3,3,3-tetrafluoro-1,2-epoxypropane or 2,3,3,3-tetrafluoro-1,2-epoxypropane may be subjected to one or more purification steps. The purification may be achieved, for example, by separation of the desired product(s) or reagents by one or more distillation, condensation or phase separation steps and/or by treatment with an acid/solvent mixture such as hydrochloric acid with acetone or methanol, followed by washing with water. Any epoxide that remains unreacted can be recycled back into the reaction.

Typically, the polymerisation is terminated by treatment with a suitable solvent such as methanol or acetone, containing a small portion (such as from about 0.1% to about 10%) of acid, such as hydrochloric acid. The precipitated polymer is then filtered washed and dried. Precipitation can be aided by the addition of water, such as deionised water).

The polymerisation reaction typically converts at least about 15% of the starting oxide into the partially fluorinated polyether polymer, preferably at least about 40%, for example, about 80%.

The polymerisation reaction is typically conducted in the liquid phase at atmospheric pressure. A temperature of from about −50° C. to about 100° C. may be used, e.g. from about −5° C. to about 90° C., such as about 80° C. or from 0 to 5° C. Lower and higher temperatures may be used. Typically, lower or higher temperatures are used if the reaction pressure is higher or lower than atmospheric pressure.

Any suitable solvent may be used or the reaction can be conducted in the absence of any solvent. By suitable we mean a solvent in which the reactants dissolve. The additional solvent should be stable to the polymerisation reaction and should not react with either the reactants or products within the taught ranges of temperature, pressure etc.

Persons skilled in the art will appreciate that these partially fluorinated polyethers can be co-polymerised with each other and/or with other epoxides of fluoroolefins, for example, 1,1,1-trifluoro-1,2-epoxypropane, 1,1,1,2,3,3-hexafluoro-1,2-epoxypropane, ethylene oxide and propylene oxide.

The partially fluorinated polyethers may be obtained via a process in which the reaction to form 2,3,3,3-tetrafluoro-1,2-epoxypropane or 1,3,3,3-tetrafluoro-1,2-epoxypropane and the reaction to form the partially fluorinated polyether take place in the same reaction vessel.

As an example, ring closing of 2-bromo-1,1,1,2-tetrafluoropropan-3-ol or 2-bromo-1,1,1,3-tetrafluoropropan-3-ol with sodium or potassium hydroxide (for example aqueous sodium or potassium hydroxide) to form 2,3,3,3-tetrafluoro-1,2-epoxypropane or 1,3,3,3-tetrafluoro-1,2-epoxypropane may be accompanied by in situ polymerisation to poly(2,3,3,3-tetrafluoro-1,2-epoxypropane) or poly(1,3,3,3-tetrafluoro-1,2-epoxypropane). For such a "one-pot" reaction, a temperature of from about −50° C. to about 100° C. may be used, e.g. from about −5° C. to about 90° C., such as about 80° C. or from 0 to 5° C. Lower and higher temperatures may be used. Typically, lower or higher temperatures are used if the reaction pressure is higher or lower than atmospheric pressure.

Polymeric species of the invention derived from 1234yf or 1234ze have been found to be soluble in 1234yf and 1234ze and are suitable for use in lubricant compositions, for example for use with refrigerant compositions comprising these HFO fluids.

The present invention also provides the use of partially fluorinated polyether polymers in an effective amount in a lubricant composition and/or a heat transfer composition due to their thermal and mechanical stability, lubricity, viscosity, pour point, anti-oxidation and anti-corrosive properties.

The present invention also provides the use of lubricant compositions and heat transfer compositions comprising partially fluorinated polyether polymers obtained using the process of the present invention in applications that require lubricant compositions and heat transfer compositions such as air conditioning, refrigeration and heat transfer systems. The partially fluorinated polyether polymers are generally miscible with lubricant materials and/or heat transfer compounds or compositions. Such lubricant compositions may contain a partially fluorinated polyether obtained in accordance with the invention in combination with one or more known lubricant materials. Likewise, such a heat transfer composition may contain a partially fluorinated polyether obtained in accordance with the invention in combination with one or more known heat transfer compounds or compositions. As an example, a partially fluorinated polyether obtained in accordance with the invention may be used in combination with 1234yf, for example in a heat transfer composition. For example, poly(2,3,3,3-tetrafluoro-1,2-epoxypropane) may be included in a composition comprising 1234yf.

BRIEF DESCRIPTION OF THE FIGURES

FIG. 6b: Shows the $^{19}$FNMR spectrum of poly(1,3,3,3-tetrafluoro-1,2-epoxy propane) in the trifluoromethyl region obtained in Example 5a.

Figure 1:
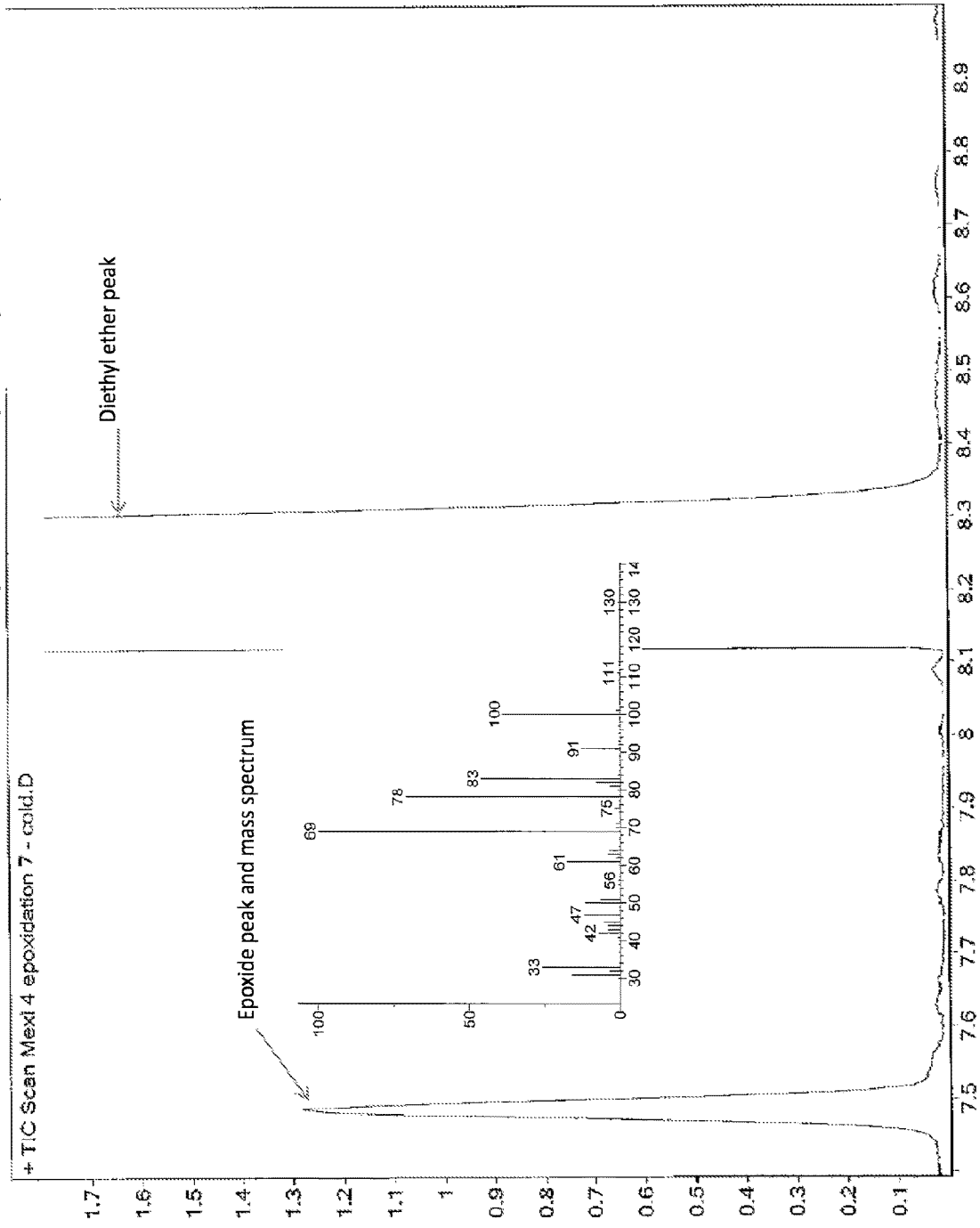
FIG. 1: Shows the GC mass spectral analysis of a sample of the reaction mixture of Example 4a taken 1 hour after the KOH addition was completed.

The invention will now be illustrated by the following non-limiting examples.

EXAMPLES

Example 1: Bromo-oxidation of Tetrafluoropropene to Form acetoxy-bromo-tetrafluoropropane: Synthesis of 3-acetoxy-2-bromo-1,1,1,2-tetrafluoropropane N-bromosuccinimide (57.2 g, 0.322 mol) was added to a 500 mL flask fitted with a condenser and thermometer. Excess concentrated acetic acid (247 mL) and concentrated sulphuric acid (0.1 equivalents, 0.0322 mol) were added at room temperature. The mixture was stirred and heated to 80° C. 1234yf was then bubbled intermittently into the solution from a pressure cylinder via a flow controller, over a 5 day period until the reaction had turned a very pale yellow. Once the reaction had cooled to 60° C. it was transferred to a separating funnel and diluted with deionised water. The clear oil was separated, and the aqueous layer was washed twice with ether. The combined organics were washed with saturated $NaHCO_3$, dried with $MgSO_4$, filtered under vacuum and concentrated affording the acetyl-bromohydrin in 21% yield (25.94 g, 0.103 mol) $C^{13}$NMR (DMSO): δ=168.9, 120.9, 98.6, 63.0, 20.5; $F^{19}$NMR (DMSO): δ=0.5, −58.1 MS: m/z 43.0, 73.0, 173.0, 253.0

Example 2: Hydrolysis of acetoxy-bromo-tetrafluoropropane to Form bromo-tetrafluoropropanol: Synthesis of 2-bromo-1,1,1,2-tetrafluoropropan-3-ol Concentrated sulphuric acid (3.4 mL, 0.0638 mol) and deionised water (34.4 mL) were added to a 50 mL three-necked round-bottom flask fitted with a condenser. 3-Acetoxy-2-bromo-1,1,1,2-tetrafluoropropane (12.84 g, 0.051 mol) was added with stirring at room temperature. The reaction was heated to reflux for 24 hours. Once cooled the contents were transferred to a separating funnel and extracted twice with ether, the combined organics were washed with saturated $NaHCO_3$, dried with $NaSO_4$, filtered and concentrated affording the alcohol in 68% yield (7.3 g, 0.0346 mol). $C^{13}$NMR (DMSO): δ=120.6, 101.1, 64.0; $F^{19}$NMR (DMSO): δ=0.03, −58.2; MS: m/z 69.0, 159.9, 189.9, 209.9.

Reference Example 3: Ring Closing of Bromo-Fluoropropanol to Form Fluorinated Epoxypropane: Synthesis of 1,1,1-trifluoro-1,2-epoxypropane 2-bromo-1,1,1-trifluoropropan-3-ol (10 g, 0.0524 mol) was placed in a 2-necked round bottom flask fitted with a distillation set up and then heated to 95° C. Sodium hydroxide (3 g, 0.0754 mol) was dissolved in water (12 g) at 0° C. with stirring. Once the solution was homogenous it was then added dropwise to the 2-bromo-1,1,1-trifluoropropan-3-ol with rapid stirring via dropping funnel. As the head temperature reached 60° C. clear liquid was collected in a receiver flask (4.2 g). GC area %: 1,1,1-trifluoro-1,2-epoxypropane (52%), 2-bromo-3,3,3-trifluoropropene+ethyl ether (26%), 3-acetoxy-2-bromo-1,1,1-trifluoropropane (7%), acetone (2%), unknown (13%).

Example 4a: Ring Closing of 1,1,1,2-tetrafluoro-2-bromopropanol to Form 2,3,3,3-tetrafluoro-1,2-epoxypropane 1,1,1,2-tetrafluoro-2-bromopropanol (20 g, 0.095 mol) was placed in a 3 necked round bottomed flask along with diethyl ether (40 g). This solution was stirred and cooled to between 0-5° C. in an ice bath and then aqueous potassium hydroxide (6.26 g KOH in 13 g water) was added dropwise over approximately 1 hour. The mixture was stirred for a further 7 hours. A sample was withdrawn 1 hour after the KOH addition was complete and analysed by GC-MS. The presence of 2,3,3,3-tetrafluoro-1,2-epoxy propane in the reaction mixture was confirmed based on mass spectral analysis of the species that eluted prior the diethyl ether solvent, see FIG. 1.

Example 4b: Ring Closing of 1,1,1,2-tetrafluoro-2-bromopropanol to Form 2,3,3,3-tetrafluoro-1,2-Epoxy Propane and its In Situ Polymerisation to poly (3,3,3,2-tetrafluoro-1,2-epoxy Propane)

Figure 2:
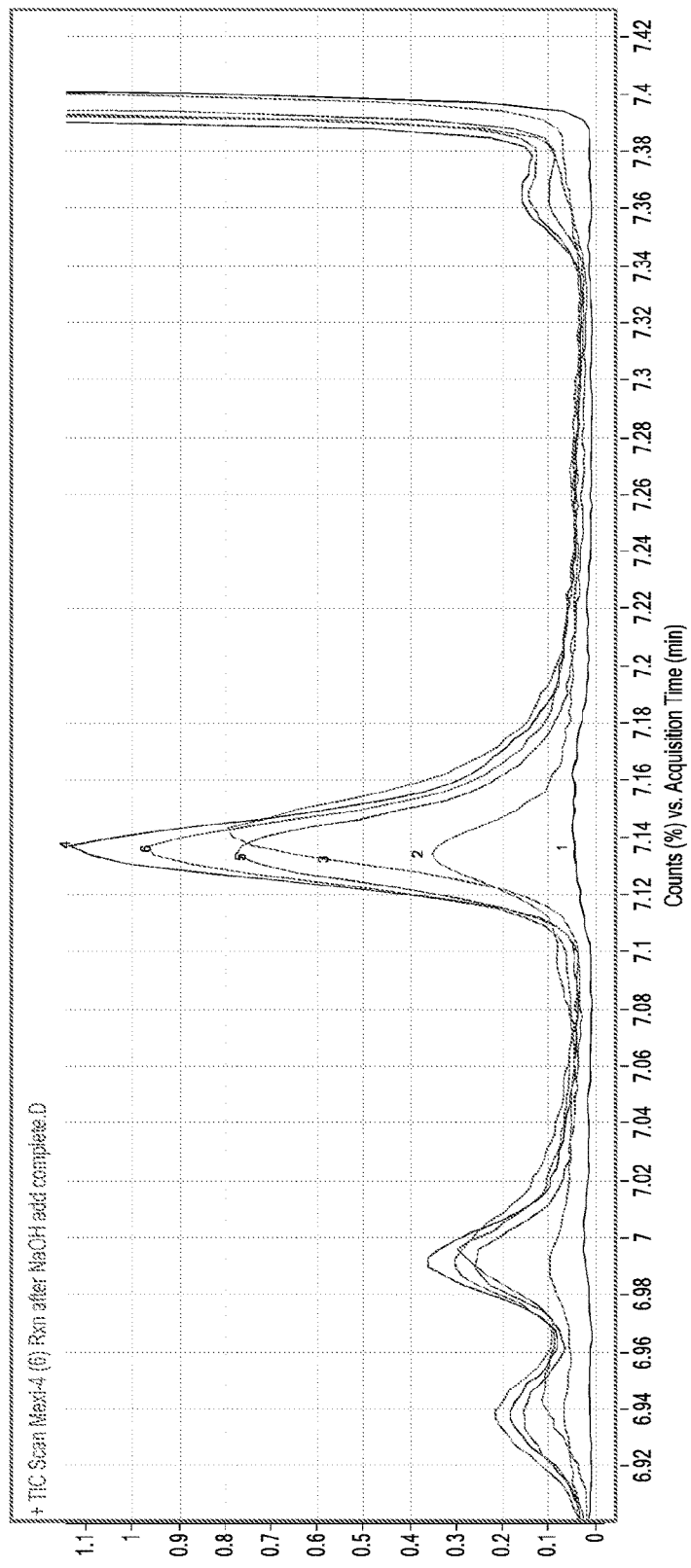
FIG. 2: Shows the region in the GC mass spectral traces where 2,3,3,3-tetrafluoro-1,2-epoxy propane eluted, sampled at intervals during the progress of the reaction.
Figure 3:
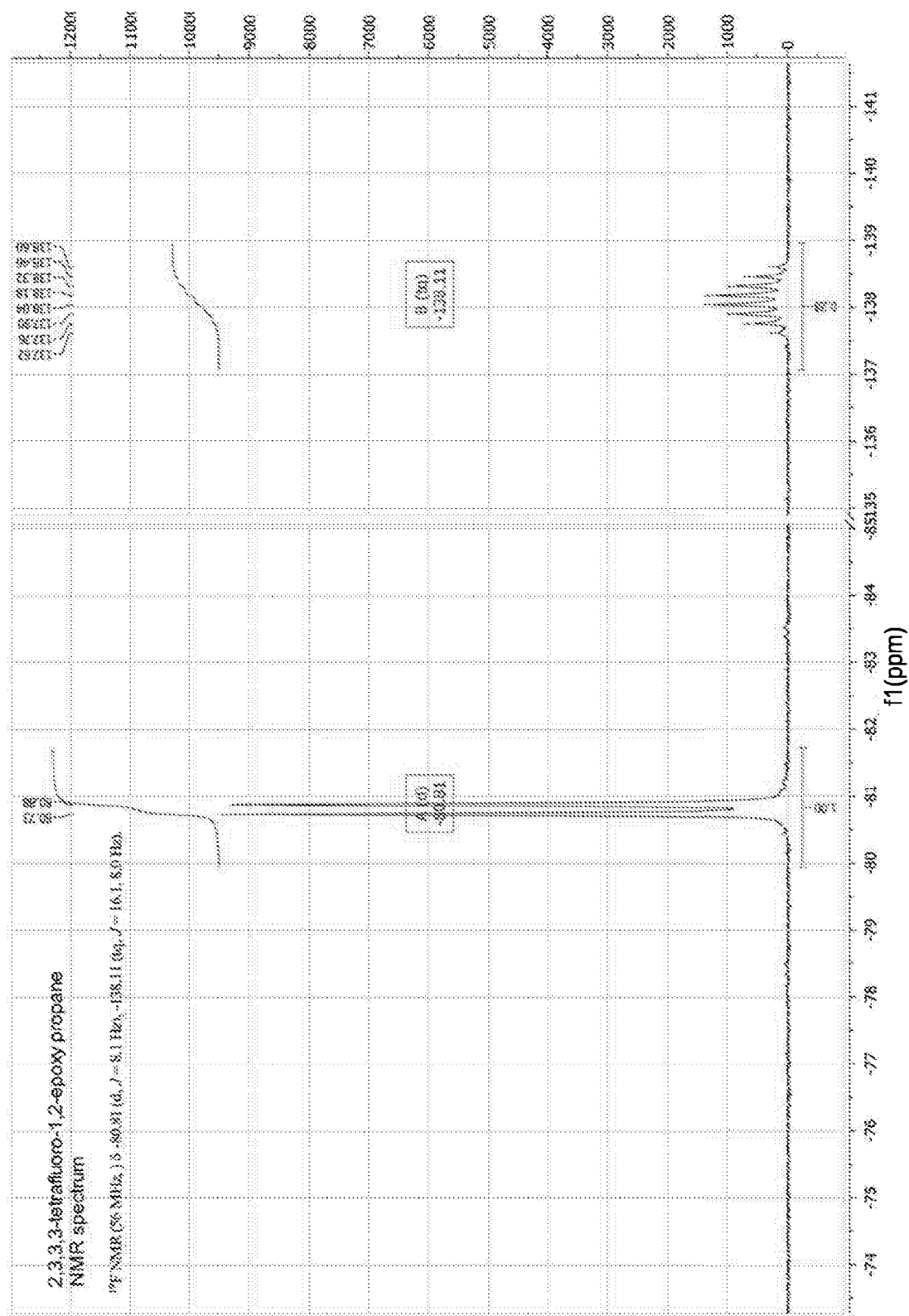
FIG. 3: Shows the $^{19}$FNMR spectrum of 2,3,3,3-tetrafluoro-1,2-epoxy propane obtained in Example 4b.

1,1,1,2-tetrafluoro-2-bromopropanol (8 g, 0.038 mol) was placed in a 3 necked round bottomed flask along with petroleum ether (40-60, 21 g) and 2-3 drops of Aliquat 336. The solution was brought to reflux (45° C.) and then aqueous sodium hydroxide (1.6 g NaOH in 20 g water) was added dropwise over approximately 1 hour. The mixture was kept at reflux for a further 6 hours and samples of the organic layer were periodically withdrawn for analysis by GC-MS and $^{19}$F NMR spectroscopy. FIG. 2 shows the region in the GC traces where 2,3,3,3-tetrafluoro-1,2-epoxy propane eluted. At the end of the experiment unreacted 2,3,3,3-tetrafluoro-1,2-epoxy propane in petroleum ether solution was obtained by distillation from the reaction mixture and was analysed by $^{19}$F NMR spectroscopy. The $^{19}$F NMR spectrum of 2,3,3,3-tetrafluoro-1,2-epoxy propane is shown in FIG. 3.

By these methods it was shown that the desired product 2,3,3,3-tetrafluoro-1,2-epoxy propane was formed and built up in the petroleum ether layer but under the high temperature/basic conditions that prevailed began to polymerise and form poly(2,3,3,3-tetrafluoro-1,2-epoxy propane) in situ.

Figure 4:
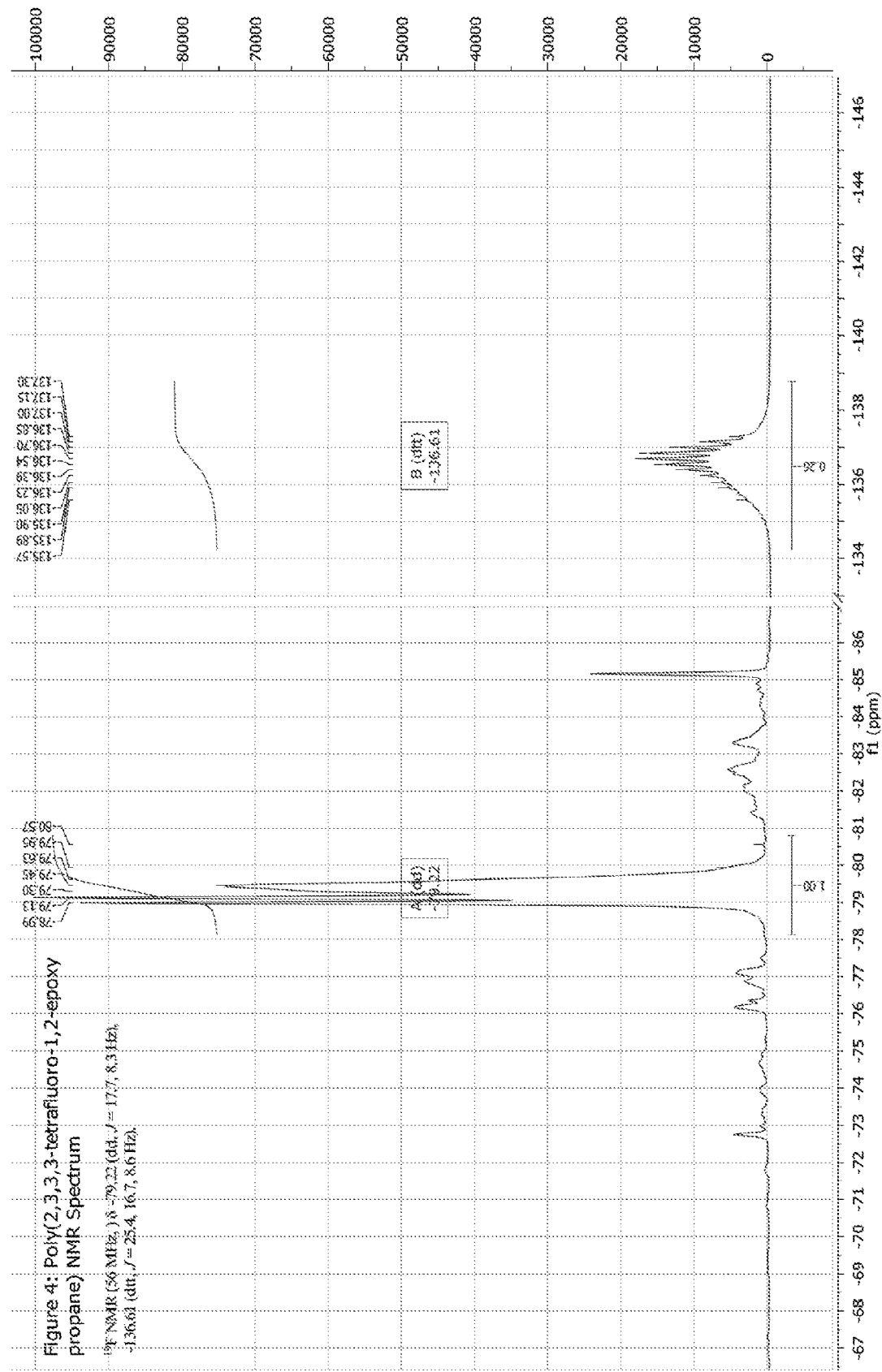
FIG. 4: Shows the $^{19}$FNMR spectrum of poly(2,3,3,3-tetrafluoro-1,2-epoxy propane) obtained in Example 4b.

The poly(2,3,3,3-tetrafluoro-1,2-epoxy propane) product was obtained from the reaction mixture distillation residue as a viscous yellow oil following water washing and extraction into dichloromethane, yield 3.24 g (66%). The $^{19}$F NMR spectrum of the polymeric product is illustrated in FIG. 4, which shows broad, complex signals characteristic of polymeric materials.

The resulting polymeric oil was found to be soluble in 1234yf and E-1234ze, confirming its utility in heat transfer compositions comprising 1234yf and/or E-1234ze.

Figure 5A:
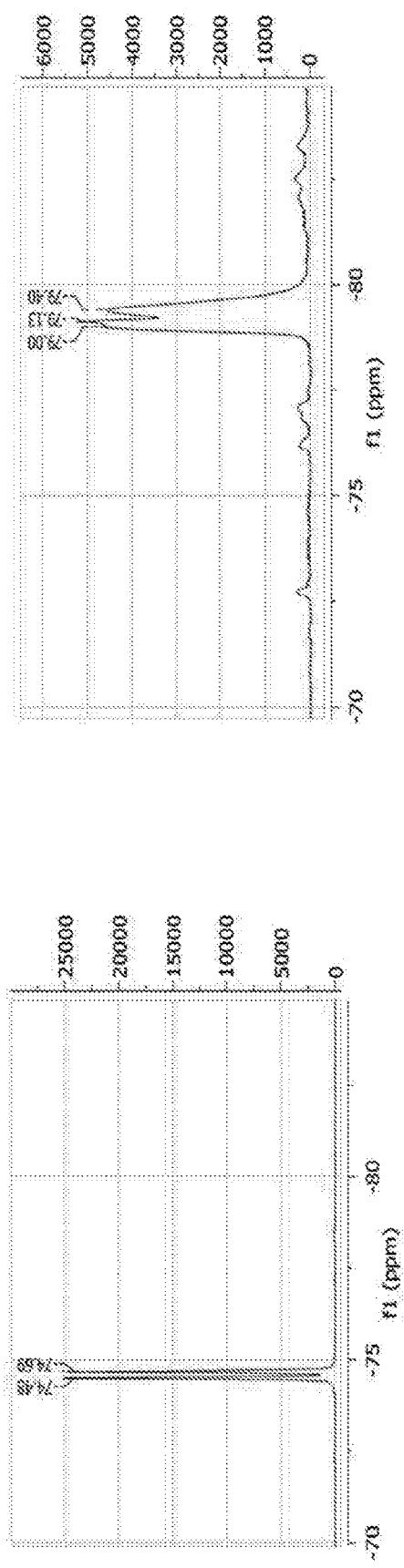
FIG. 5a: Shows the regions of the $^{19}$FNMR spectrum of poly(2,3,3,3-tetrafluoro-1,2-epoxy propane) obtained in Example 4b in 1234yf that contained resonances associated with the $CF_3$ groups, the spectra of 1234yf and the polymer alone are included for reference.
Figure 5A:
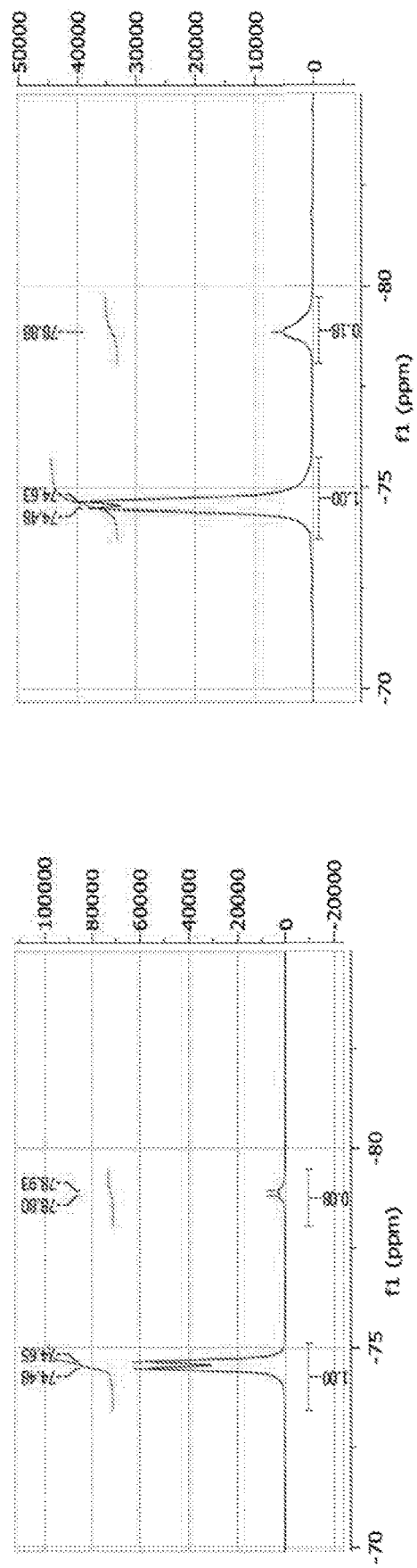

Solutions of poly(2,3,3,3-tetrafluoro-1,2-epoxy propane) in 1234yf were prepared and analysed by $^{19}$F NMR spectroscopy, the region of their NMR spectra that contained resonances associated with the $CF_3$— groups in these species are illustrated in FIG. 5*a*. For reference, spectra of 1234yf and the polymer alone are also included.

Figure 5B:
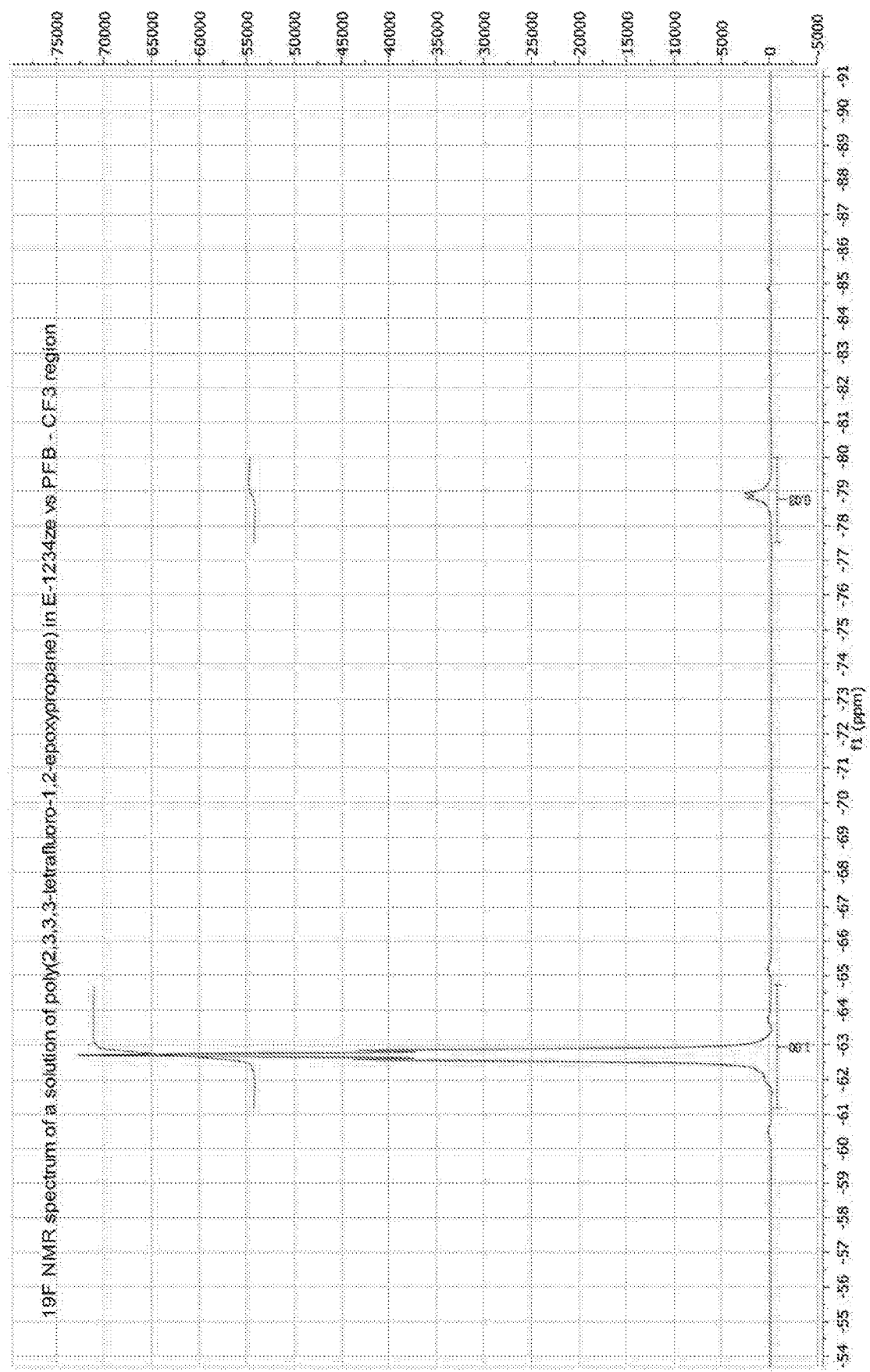
FIG. 5b: Shows the $^{19}$FNMR spectrum of poly(2,3,3,3-tetrafluoro-1,2-epoxy propane) obtained in Example 4b in E-1234ze.

Solutions of poly(2,3,3,3-tetrafluoro-1,2-epoxy propane) in E-1234ze were prepared and analysed by $^{19}$F NMR spectroscopy, as showed in FIG. 5*b*.

Example 5: Polymerisation of 1,3,3,3-Tetrafluoro-1,2-epoxy Propane

5a: Potassium t-Butoxide Initiator

Figure 6A:
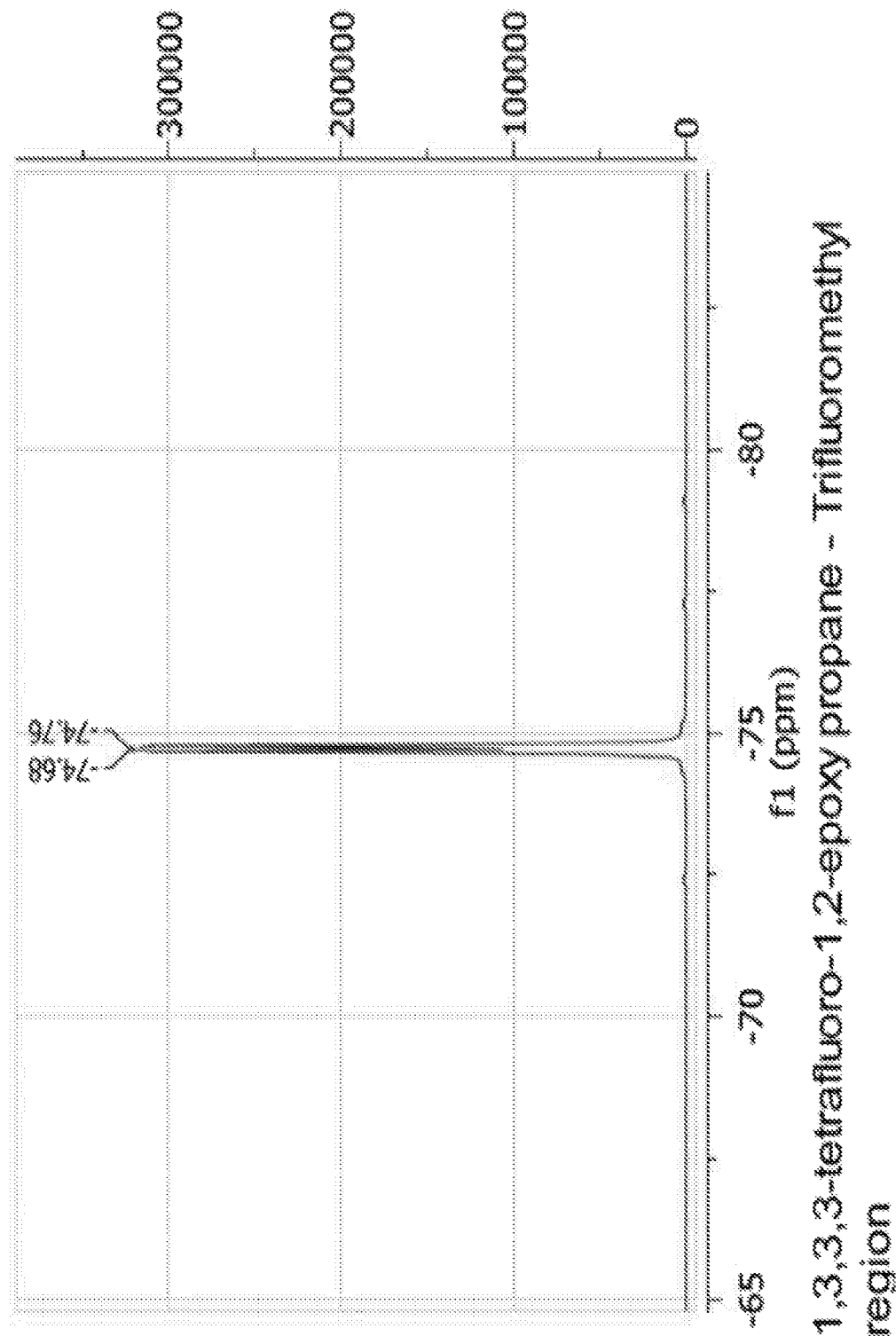
FIG. 6a: Shows the $^{19}$FNMR spectrum of 1,3,3,3-tetrafluoro-1,2-epoxy propane in the trifluoromethyl region as used in Examples 5a and 5b.
Figure 6B:
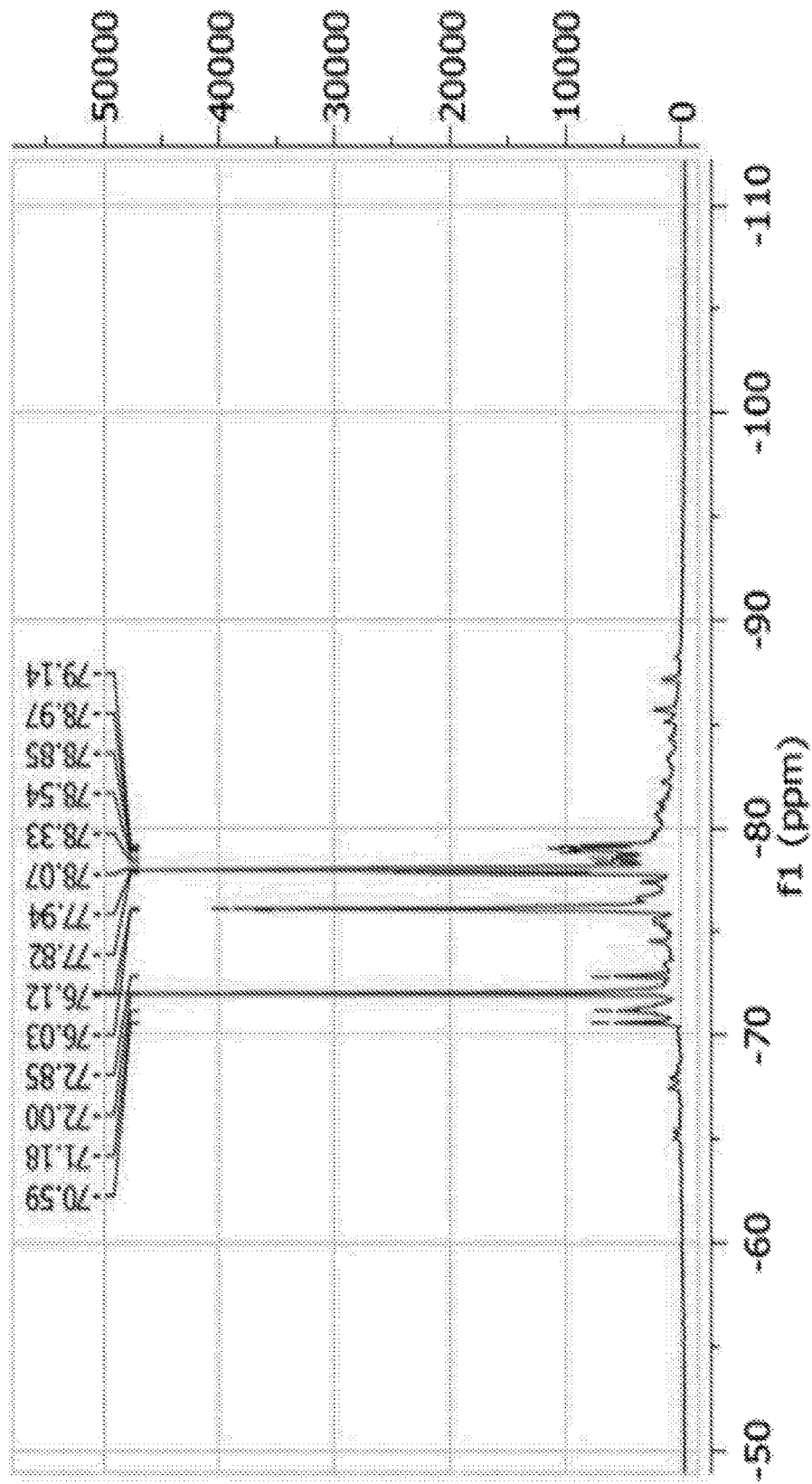

The initiator (2 g) was weighed into a 100 ml capacity autoclave along with solvent (THF, 52 g) and 1,3,3,3-Tetrafluoro-1,2-epoxy propane (30 g). The autoclave was sealed and the contents heated to 100° C. with stirring for 7 hours. After cooling the contents were recovered and the solvent removed in vacuo. The residual oil was dissolved in dichloromethane and the solution washed with water before being dried over anhydrous sodium sulphate. Removal of the solvent in vacuo afforded a viscous yellow oil. The $^{19}$F NMR spectrum of the oil is illustrated in FIG. 6*b* along with that of the starting material for comparison.

Figure 6C:
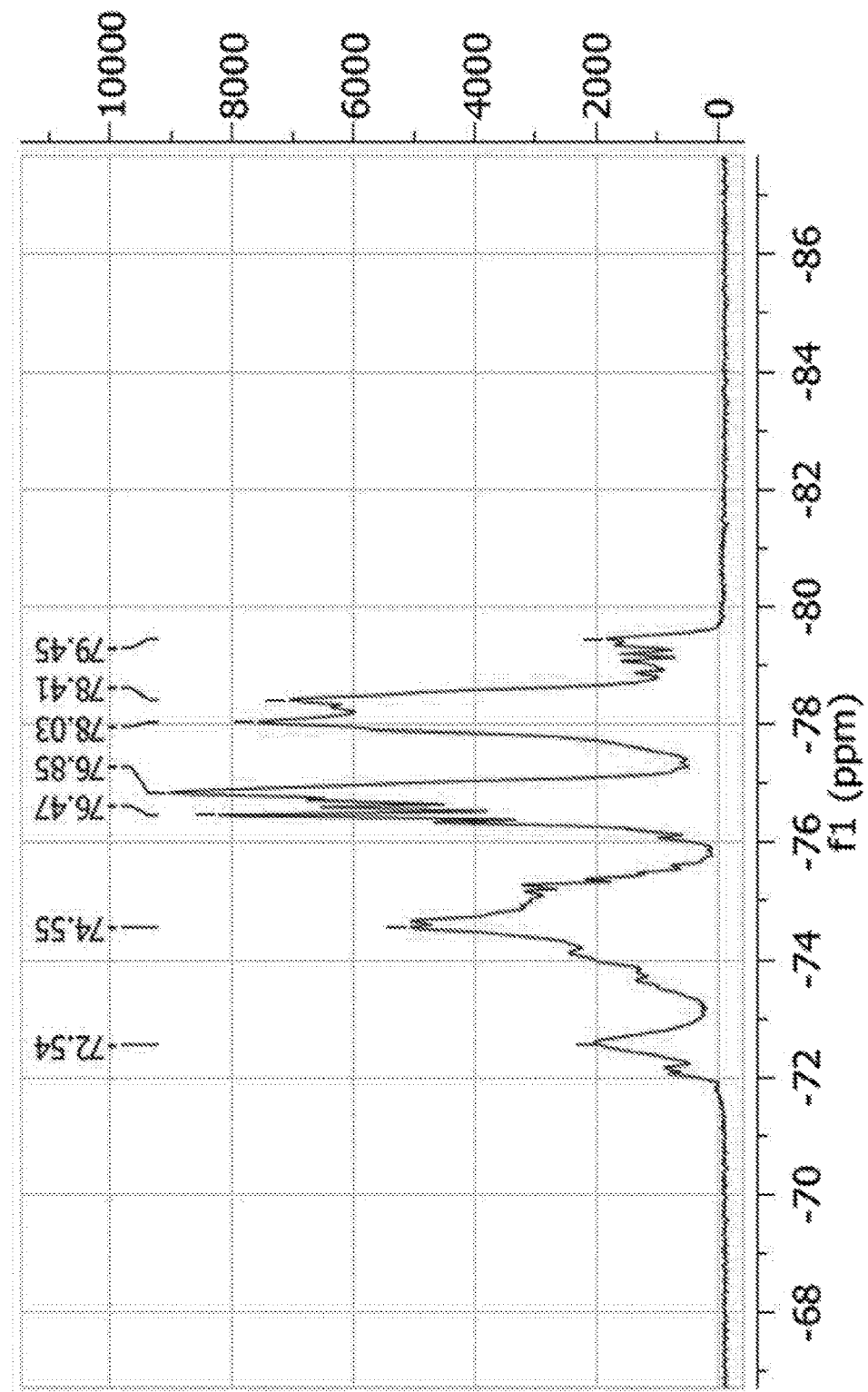
FIG. 6c: Shows the $^{19}$FNMR spectrum of poly(1,3,3,3-tetrafluoro-1,2-epoxy propane) in the trifluoromethyl region obtained in Example 5b.

5b: Sulphuric Acid Initiator 1,3,3,3-Tetrafluoro-1,2-epoxy propane (23 g) was added to a 50 ml round bottomed flask equipped with a dry ice condenser containing the initiator (98% wt, 1 ml). The resulting mixture was stirred for 7 hours and then the excess epoxide was distilled off. The resulting oily residue was washed with water and extracted into diethyl ether. The ether solution was dried over anhydrous sodium sulphate and the ether removed in vacuo yielding a viscous red coloured oil. The $^{19}$F NMR spectrum of the oil is illustrated in FIG. 6*c* along with that of the starting material for comparison.

The invention claimed is:

1. A method for preparing a tetrafluoro-1,2-epoxypropane comprising reacting a 3-acetoxy-2-bromo-tetrafluoropropane with an alkaline or alkaline earth metal hydroxide solution to provide a tetrafluoro-1,2-epoxypropane.

2. The method according to claim 1, wherein the 3-acetoxy-2-bromo-tetrafluoropropane is 3-acetoxy-2-bromo-1,1,1,2-tetrafluoropropene or 3-acetoxy-2-bromo-1,1,1,2-tetrafluoropropene, which is reacted with sodium or potassium hydroxide to form 2,3,3,3-tetrafluoro-1,2-epoxypropane or 1,3,3,3-tetrafluoro-1,2-epoxypropane.

3. The method of claim 1, wherein the alkaline metal hydroxide is sodium hydroxide.

4. The method of claim 1, wherein the alkaline metal hydroxide is potassium hydroxide.

5. A method for preparing a partially fluorinated polyether, comprising polymerising 2,3,3,3-tetrafluoro-1,2-epoxypropane or 1,3,3,3-tetrafluoro-1,2-epoxypropane to provide a partially fluorinated polyether of formula $[OCRR_1CR_2R_3]_n$, wherein R is H, $R_1$ is $CF_3$, $R_2$ is H and $R_3$ is F or R is F, $R_1$ is $CF_3$, $R_2$ is H and $R_3$ is H, wherein n is from 5 to 100.

6. The method according to claim 5, further comprising reacting a 2-bromo-tetrafluoropropan-3-ol with an alkaline or alkaline earth metal hydroxide solution to provide 2,3,3,3-tetrafluoro-1,2-epoxypropane or 1,3,3,3-tetrafluoro-1,2-epoxypropane.

7. The method of claim 6, further comprising reacting 3-acetoxy-2-bromo-1,1,1,2-tetrafluoropropene or 3-acetoxy-2-bromo-1,1,1,2-tetrafluoropropene with sulphuric acid in an aqueous solution to provide 2-bromo-1,1,1,2-tetrafluoropropan-3-ol or 2-bromo-1,1,1,3-tetrafluoropropan-3-ol.

8. The method according to claim 6, wherein the reaction to form 2,3,3,3-tetrafluoro-1,2-epoxypropane or 1,3,3,3-tetrafluoro-1,2-epoxypropane and the reaction to form the partially fluorinated polyether take place in the same reaction vessel.

9. The method according to claim 5, wherein the polymerising is initiated using a cationic initiator, an anionic initiator or an organometallic based initiator.

10. The method according to claim 9, wherein the initiator is an alkali metal tert-butoxide, sodium or potassium hydroxide, sulphuric acid, metal chloride or metal fluoride.

11. The method according to claim 10, wherein the metal fluoride is cesium fluoride.

12. The method according to claim 9, wherein the initiator is an organozinc or organoaluminium compound.

13. The method according to claim 12, wherein the initiator is selected from the group consisting of $Zn(C_2H_5)_2$, $(C_2H_5ZnOCH_3)_4$, $Zn(OCH_3)_2(C_2H_5ZnOCH_3)_6]$, $[C_2H_5ZnMP]_2[ZnMP_2]_2$, trimethylaluminium, triethylaluminium and triisobutylaluminium, wherein MP is CH3OCH2CH(CH3)O—.

14. A partially fluorinated polyether of formula $[OCRR_1CR_2R_3]_n$, wherein n is from 5 to 100, wherein R is H, $R_1$ is $CF_3$, $R_2$ is F and $R_3$ is H or R is F, $R_1$ is $CF_3$, $R_2$ is H and $R_3$ is H.

15. A lubricant composition comprising a partially fluorinated polyether according to claim 14.

16. A heat transfer composition comprising a partially fluorinated polyether according to claim 14.

* * * * *